(12) United States Patent
Mitchell

(10) Patent No.: US 9,402,398 B2
(45) Date of Patent: Aug. 2, 2016

(54) HERBICIDAL COMPOUNDS

(71) Applicant: SYNGENTA PARTICIPATIONS AG, Basel (CH)

(72) Inventor: Glynn Mitchell, Bracknell (GB)

(73) Assignee: Syngenta Limited, Basel (CH)

( * ) Notice: Subject to any disclaimer, the term of this patent is extended or adjusted under 35 U.S.C. 154(b) by 8 days.

(21) Appl. No.: 14/386,564

(22) PCT Filed: Mar. 19, 2013

(86) PCT No.: PCT/EP2013/055626
§ 371 (c)(1),
(2) Date: Sep. 19, 2014

(87) PCT Pub. No.: WO2013/139760
PCT Pub. Date: Sep. 26, 2013

(65) Prior Publication Data
US 2015/0072860 A1  Mar. 12, 2015

(30) Foreign Application Priority Data
Mar. 20, 2012 (GB) .................................. 1204893.0
Mar. 29, 2012 (GB) .................................. 1205662.8

(51) Int. Cl.
*A01N 43/713* (2006.01)
*A01N 43/653* (2006.01)
*C07D 401/14* (2006.01)
*C07D 403/12* (2006.01)

(52) U.S. Cl.
CPC ............ *A01N 43/713* (2013.01); *A01N 43/653* (2013.01); *C07D 401/14* (2013.01); *C07D 403/12* (2013.01)

(58) Field of Classification Search
CPC . A01N 43/653; A01N 43/713; C07D 401/14; C07D 403/12
See application file for complete search history.

(56) References Cited

U.S. PATENT DOCUMENTS

2014/0371067 A1* 12/2014 Mitchell .............. A01N 43/713
504/103
2015/0065345 A1* 3/2015 Mitchell .............. C07D 401/12
504/103

FOREIGN PATENT DOCUMENTS

WO  2012028579  3/2012

OTHER PUBLICATIONS

Database Registry, Chemical Abstracts Service, Columbus, Ohio, US; Apr. 22, 2011; retrieved from STN, CHEMCATS File, Database accession No. RN 128-4199-79-6.*
Database Registry, Chemical Abstracts Service, Columbus, Ohio, US; Apr. 4, 2011; retrieved from STN, CHEMCATS File, Database accession No. RN 127-4674-47-3.*
Database Registry, Chemical Abstracts Service, Columbus, Ohio, US; Apr. 22, 2011, retrieved from STN, Database accession No. RN 128-4199-79-6.
Database Registry, Chemical Abstracts Service, Columbus, Ohio, US; Apr. 4, 2011, retrieved from STN, Database accession No. RN 1274674-47-3.
International Search Report for International Application No. PCT/EP2013/055626, completed May 14, 2013.

* cited by examiner

*Primary Examiner* — Jane C Oswecki
(74) *Attorney, Agent, or Firm* — James Cueva

(57) ABSTRACT

The present invention relates to compounds of Formula (I); or an agronomically acceptable salt of said compounds wherein $A^{1a}$, $A^{1b}$, $A^2$, $A^3$, $A^4$, X, $R^1$ and $R^2$ are as defined herein. The invention further relates to herbicidal compositions which comprise a compound of Formula (I), and to their use for controlling weeds, in particular in crops of useful plants.

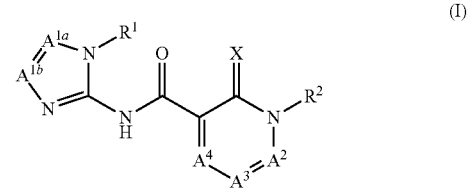

12 Claims, No Drawings

HERBICIDAL COMPOUNDS

This application is a 371 of International Application No. PCT/EP2013/055626 filed Mar. 19, 2013, which claims priority to EP 12048930 filed Mar. 20, 2012, and EP 12056628 filed Mar. 29, 2012, the contents of which are incorporated herein by reference.

The present invention relates to novel herbicidal compounds, to processes for their preparation, to herbicidal compositions which comprise the novel compounds, and to their use for controlling weeds, in particular in crops of useful plants, or for inhibiting plant growth.

Herbicidal N-(Tetrazol-5-yl) and N-(Triazol-5-yl) arylcarboxamides are known from WO2012/028579. The present invention relates to the provision of further such compounds. Thus, according to the present invention there is provided a compound of Formula (I):

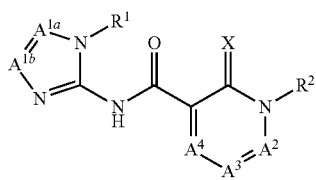

or an agronomically acceptable salt thereof,
wherein:—
X is O or S;
$A^{1a}$ and $A^{1b}$ are independently selected from CH and N, wherein $A^{1a}$ and $A^{1b}$ are not both CH;
$A^2$ is N;
$A^3$ is $CR^4$;
$A^4$ is $CR^5$;
$R^1$ is selected from the group consisting of hydrogen, $C_1$-$C_6$alkyl-, $C_1$-$C_6$ haloalkyl- and $C_1$-$C_6$alkoxy-$C_1$-$C_3$alkyl-;
$R^2$ is selected from the group consisting of hydrogen, $C_1$-$C_6$alkyl, $C_1$-$C_6$haloalkyl, $C_1$-$C_3$alkoxy-$C_1$-$C_3$ alkyl, $C_1$-$C_3$ alkoxy-$C_2$-$C_3$alkoxy-$C_1$-$C_3$-alkyl, $C_1$-$C_3$haloalkoxy-$C_1$-$C_3$-alkyl, ($C_1$-$C_3$ alkylsulfonyl-$C_1$-$C_3$ alkylamino)-$C_1$-$C_3$ alkyl, ($C_1$-$C_3$ alkylsulfonyl)-$C_1$-$C_3$alkyl, $C_3$-$C_4$ cycloalkylamino)-$C_1$-$C_3$alkyl, $C_1$-$C_6$alkylcarbonyl-$C_1$-$C_3$alkyl, $C_3$-$C_6$cycloalkyl-$C_2$-$C_6$alkenyl, $C_2$-$C_6$alkynyl, $C_2$-$C_6$-alkenyl, $C_2$-$C_6$-haloalkenyl, cyano-$C_1$-$C_6$-alkyl, arylcarbonyl-$C_1$-$C_3$-alkyl, aryl-$C_1$-$C_6$alkyl, aryloxy-$C_1$-$C_6$alkyl (wherein said aryl groups may be optionally substituted with one or more substituents from the group consisting of halogen, $C_1$-$C_3$-alkoxy, $C_1$-$C_3$-alkyl, $C_1$-$C_3$ haloalkyl), and a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more substituents selected from the group consisting of nitro, cyano, halogen, $C_1$-$C_3$alkyl, $C_1$-$C_3$haloalkyl, $C_2$-$C_3$alkenyl, $C_2$-$C_3$alkynyl, $C_1$-$C_3$ alkoxy, $C_1$-$C_3$ haloalkoxy, $C_1$-$C_6$alkyl-S(O)p- and $C_1$-$C_6$haloalkyl-S(O)p-;
$R^4$ is selected from the group consisting of hydrogen, hydroxyl, halogen, $C_1$-$C_6$alkyl, $C_1$-$C_6$haloalkyl, $C_1$-$C_6$alkoxy-$C_1$-$C_6$alkyl, $C_1$-$C_6$haloalkoxy-$C_1$-$C_6$alkyl, $C_1$-$C_6$alkoxy-$C_1$-$C_6$alkoxy-$C_1$-$C_6$alkyl, $C_1$-$C_6$alkoxy, $C_1$-$C_6$haloalkoxy, $C_1$-$C_6$alkoxy-$C_2$-$C_6$alkoxy, $C_1$-$C_6$alkylamino, $C_1$-$C_6$dialkylamino-, cyano, $C_1$-$C_6$alkyl-S(O)p- and $C_1$-$C_6$haloalkyl-S(O)$_p$—;
$R^5$ is selected from the group consisting of hydrogen, hydroxyl, $C_1$-$C_6$ alkyl, $C_1$-$C_6$haloalkyl and $C_1$-$C_6$alkoxy-$C_1$-$C_3$alkyl; and
p=0, 1 or 2.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents present on the same carbon atom may be joined to form a spiro group. Thus, the methyl groups present in two methoxy substituents may be joined to form a spiro 1,3 dioxolane substituent, for example. Such a possibility is within the scope of the present invention.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S-(alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)-(alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$-(alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamino or a butylamino isomer. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

In a particular aspect of the present invention there is provided a compound of Formula (I), wherein $A^{1a}$ is CH or N and $A^{1b}$ is N.

In another aspect of the present invention there is provided a compound of Formula (I), wherein $A^{1a}$ is N and $A^{1b}$ is CH or N.

In a preferred embodiment of the invention X is O.

In a preferred embodiment of the present invention, $A^{1a}$ and $A^{1b}$ are both N.

In another preferred embodiment, $R^1$ is methyl or ethyl, preferably methyl.

In another preferred embodiment, $R^2$ is selected from the group consisting of $C_1$-$C_6$alkyl, $C_1$-$C_3$alkoxy-$C_1$-$C_3$ alkyl, $C_1$-$C_3$haloalkoxy-$C_1$-$C_3$-alkyl, phenyl and a 5 or 6 membered heteroaromatic ring system containing from 1 to 4 heteroatoms each independently selected from the group consisting of nitrogen, oxygen and sulphur; the phenyl or 5 or 6 heteroaromatic ring system being optionally substituted by one or more substituents selected from the group consisting of nitro, cyano, halogen, $C_1$-$C_3$alkyl, $C_1$-$C_3$haloalkyl, $C_2$-$C_3$alkenyl, $C_2$-$C_3$alkynyl, $C_1$-$C_3$ alkoxy, $C_1$-$C_3$ haloalkoxy, $C_1$-$C_6$alkyl-S(O)p- and $C_1$-$C_6$haloalkyl-S(O)p-.

In a more preferred embodiment, $R^2$ is selected from the group consisting of $C_1$-$C_6$alkyl-, $C_1$-$C_3$alkoxy-$C_1$-$C_3$alkyl-, $C_1$-$C_6$alkylcarbonyl-$C_1$-$C_3$alkyl, benzyl-, pyridyl and phenyl-, the benzyl, pyridyl and phenyl groups being optionally substituted by one or more substituents selected from the group consisting of cyano, halogen, $C_1$-$C_3$alkyl-, $C_1$-$C_3$haloalkyl-, $C_2$-$C_3$alkenyl-, $C_1$-$C_3$alkoxy- and $C_1$-$C_3$haloalkoxy-.

In an even more preferred embodiment, $R^2$ is selected from the group consisting of $C_1$-$C_3$alkoxy-$C_1$-$C_3$alkyl- (preferably methoxyethyl-), pyridyl and phenyl-, the pyridyl and phenyl groups being optionally substituted by one or more substituents selected from the group consisting of cyano, halogen (preferably fluorine, chlorine or bromine), $C_1$-$C_3$alkyl- (preferably methyl or ethyl), $C_2$-$C_3$alkenyl-(preferably vinyl), $C_2$-$C_3$alkynyl (preferably ethynyl) and $C_1$-$C_3$alkoxy- (preferably methoxy or ethoxy).

In another embodiment $R^4$ is selected from the group consisting of hydrogen, methyl and halogen.

In another embodiment $R^5$ is hydrogen or methyl, preferably hydrogen.

Compounds of Formula I may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula I may be in equilibrium with alternative tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula I may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+fluorochloridone, I+fluoroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+triallate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096,576.

The mixing partners of the compound of Formula I may also be in the form of esters or salts, as mentioned e.g. in The Pesticide Manual, Fourteenth Edition, British Crop Protection Council, 2006.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino] benzenesulfonamide.

The safeners of the compound of Formula I may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula Ito safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from Pseudomonas fluorescens or Shewanella colwelliana, or from a plant, more particularly, derived from a monocot plant or, yet more particularly, from a barley, maize, wheat, rice, Brachiaria, Cenchrus, Lolium, Festuca, Setaria, Eleusine, Sorghum or Avena species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by Bacillus thuringiensis soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria and Sorghum, and dicotyledonous species, for example Abutilon, Amaranthus, Ambrosia, Chenopodium, Chrysanthemum, Conyza, Galium, Ipomoea, Nasturtium, Sida, Sinapis, Solanum, Stellaria, Veronica, Viola and Xanthium. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared according to the following scheme.

Scheme 1:- Reaction of an activated carboxylic acid with a 1-alkyl-5-aminotetrazole:

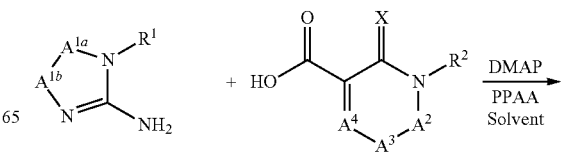

-continued

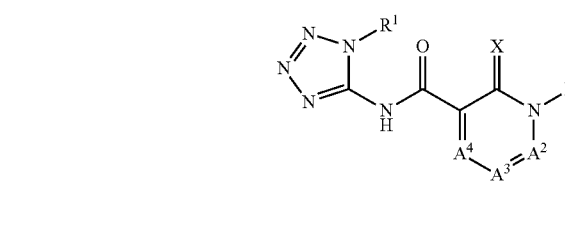

Scheme 2:- Reaction of an activated carboxylic acid with a 5-(alkylamino)tetrazole:

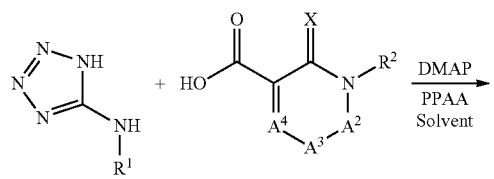

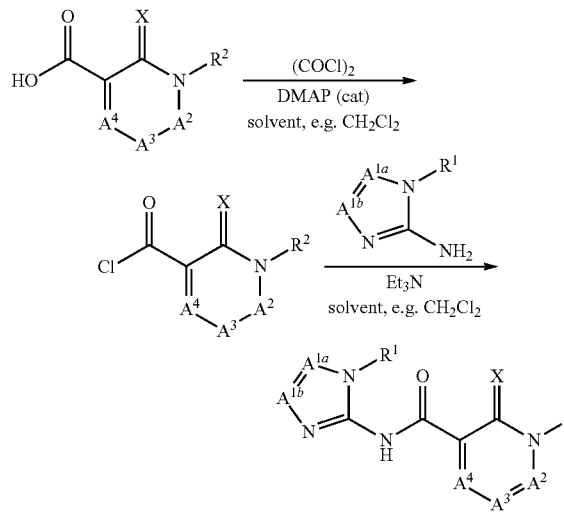

In each case, DMAP=4-dimethylaminopyridine, PPAA=1-propanephosphonic acid cyclic anhydride, and the solvent is a non-protic organic solvent such as ethyl acetate or dichloromethane.

Scheme 3: Reaction of an acid chloride with an aminotriazole or an aminotetrazole:

The carboxylic acids can be prepared by known methods, or methods analogous to known methods. Examples of such methods are given below.

In cases where $R^2$ is an aryl or heteroaryl bromide, this can be converted to the corresponding nitrile by the method shown in Scheme 4.

Scheme 4: Conversion of an aryl bromide to an aryl nitrile:

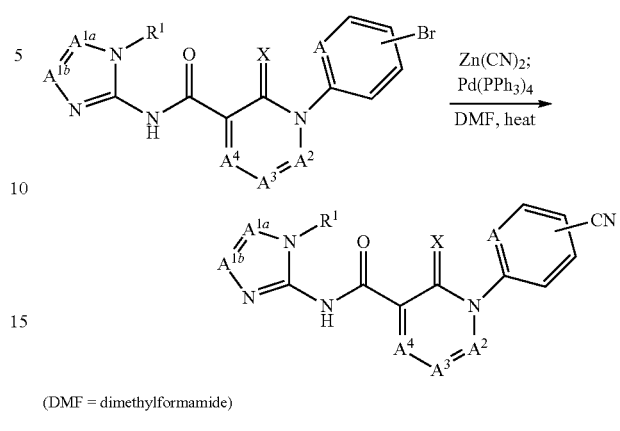

(DMF = dimethylformamide)

In cases where $R^2$ is an aryl or heteroaryl bromide, this can be converted to an acetylene by the method shown in Scheme 5. Use of a tributylstannyl $C_3$-$C_6$-acetylene in the first step results in the formation of the $C_3$-$C_6$-substituted aryl acetylene.

Scheme 5: Conversion of an aryl bromide to an acetylene:

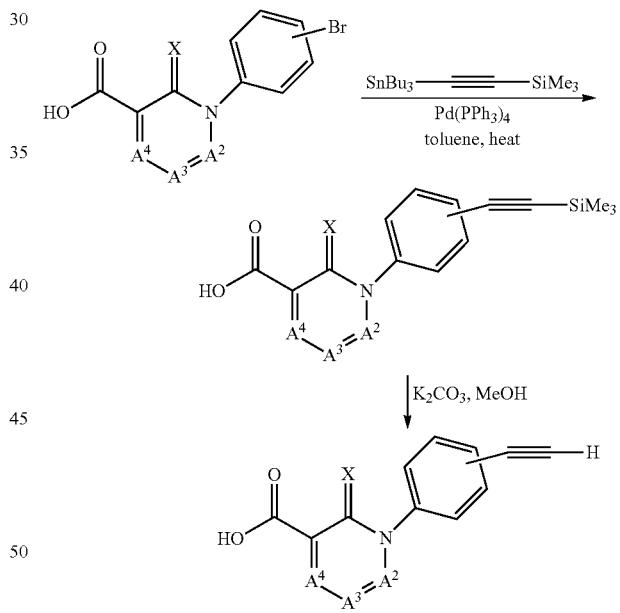

In cases where $R^2$ is an aryl or heteroaryl bromide, this can be converted to an alkene by the method shown in Scheme 6.

Scheme 6: Conversion of an aryl bromide to an alkene:

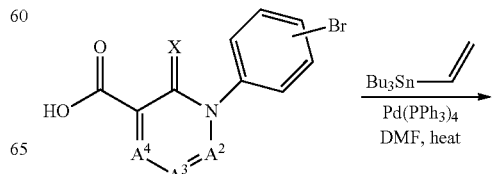

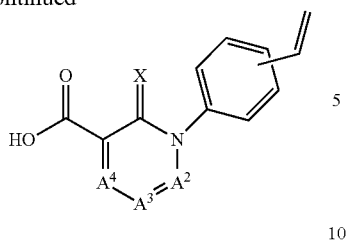

In cases where $R^2$ is alkyl, the carboxylic acid can be prepared by N-alkylation of the NH ester followed by de-esterification as shown in Scheme 7.

Scheme 7. Formation of heterocyclic carboxylic acid - N-alkylation of heterocycle (i.e. $R^2$ = (substituted)alkyl):

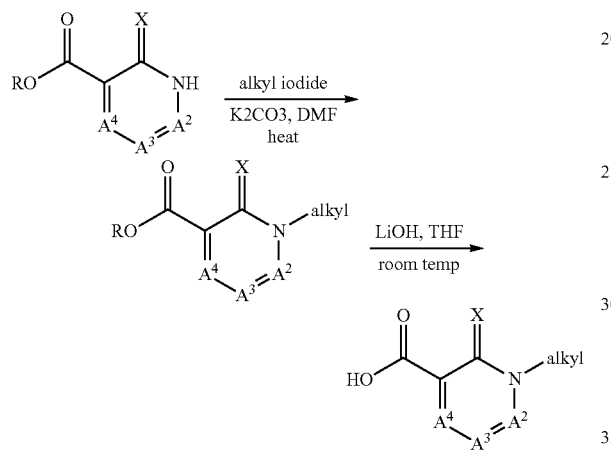

In cases where $R^2$ is aryl or heteroaryl, the carboxylic acid can be prepared by N-(hetero)arylation of the NH ester followed by de-esterification as shown in Scheme 8.

Scheme 8: Formation of heterocyclic carboxylic acid-N-arylation of heterocycle (i.e. $R^2$ = (substitutedaryl/heteroaryl):

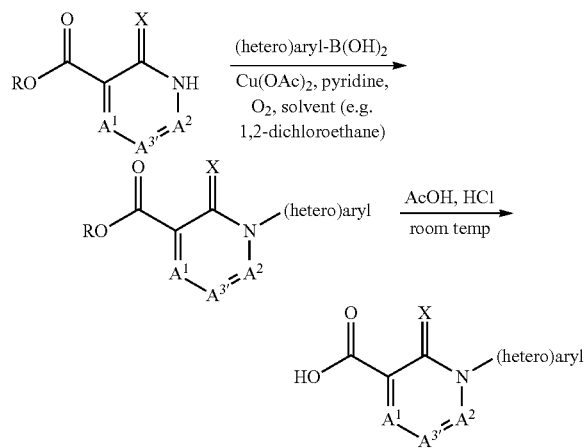

The carboxylic acids may also be prepared by ring synthesis. In cases where the ring is a pyridazinone, the ring can be constructed by the method shown in Scheme 9.

Scheme 9: Formation of heterocyclic carboxylic acid-construction of pyridazinone ring:

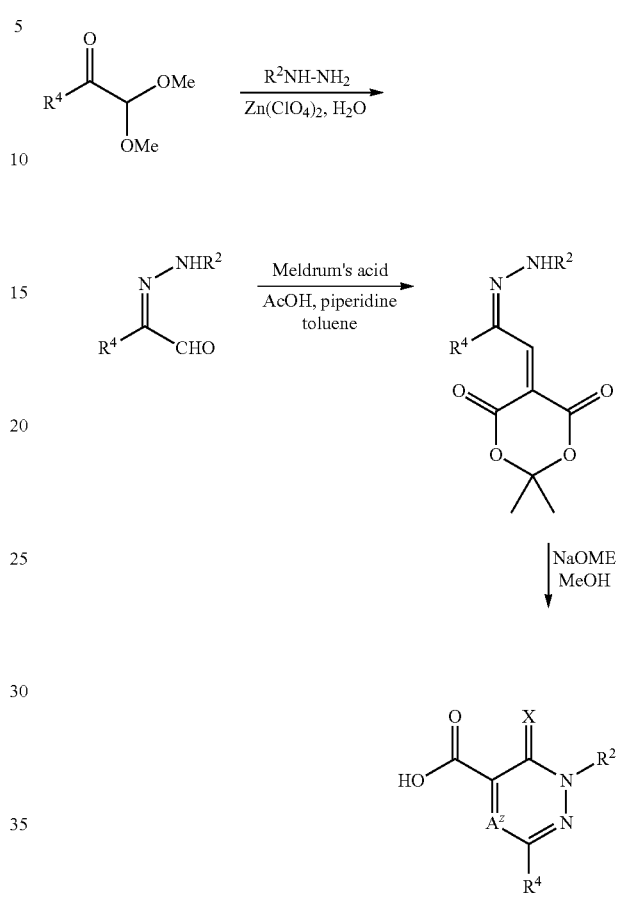

The following non-limiting examples provide specific synthesis methods for representative compounds of the present invention, as referred to in Tables 1 to 12 below.

EXAMPLE P1

Experimental Procedure for the Synthesis of Compound 1.006

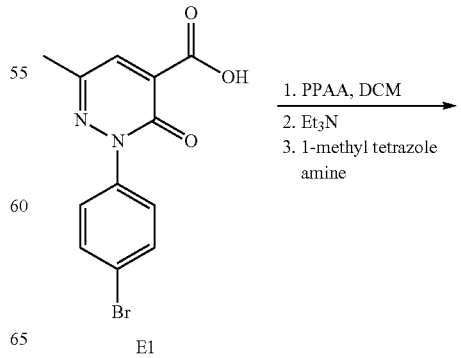

1. PPAA, DCM
2. Et₃N
3. 1-methyl tetrazole amine

E1

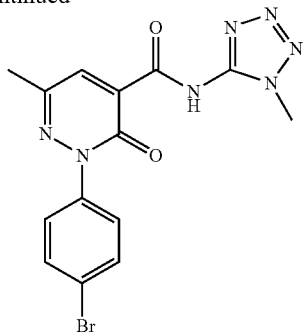

Compound 1.006

To a solution of the carboxylic acid E1 (500 mg, 1.620 mmol) and 5-amino-1-methyltetrazole (192 mg, 1.94 mmol) in HPLC grade dichloromethane (15 ml), dry triethylamine (0.661 ml, 4.80 mmol) was added dropwise at 0° C. and the reaction mixture was then stirred at RT for 10 min. PPAA (50% in ethyl acetate, 2 ml, 3.24 mmol) was then added, and stirring was continued for a further 15 hours. The reaction mixture was diluted with 30 ml dichloromethane, and the dichloromethane solution was washed with water (1×10 ml), brine (1×10 ml), dried over sodium sulfate and evaporated under reduced pressure to afford the crude product, which was purified on a Combiflash using ethyl acetate-hexane to afford the desired compound 1.006 as a white solid (160 mg). Yield: 25%.

EXAMPLE P2

Experimental Procedure for the Synthesis of Compound 1.009

STEP 1: The pyridazine E2 (10 g, 0.032 mol) was dissolved in dry DMF (100 ml) in a round bottom flask and degassed for 10 min. Then tributylvinyl tin (20 ml, 0.048 mol) was added, and the solution was degassed for a further 10 min. Then tetrakis(triphenylphosphine)palladium(0) (1.87 g, 0.0016 mol) was added and the mixture was degassed for 10 min. The reaction mixture was then heated to 90° C. with stirring for 18 h. The reaction mixture was then cooled to room temperature and basified to pH 12-13 with 1M sodium hydroxide solution, and this solution was washed with ethyl acetate. Then the aqueous phase was then acidified with 6M hydrochloric acid and extracted with ethyl acetate (150 ml×3). The combined extracts of the acidic aqueous phase extract were dried over sodium sulfate and then concentrated under reduced pressure. The resultant brown solid was triturated with methanol in hexane (10%) to afford the vinyl compound E3.

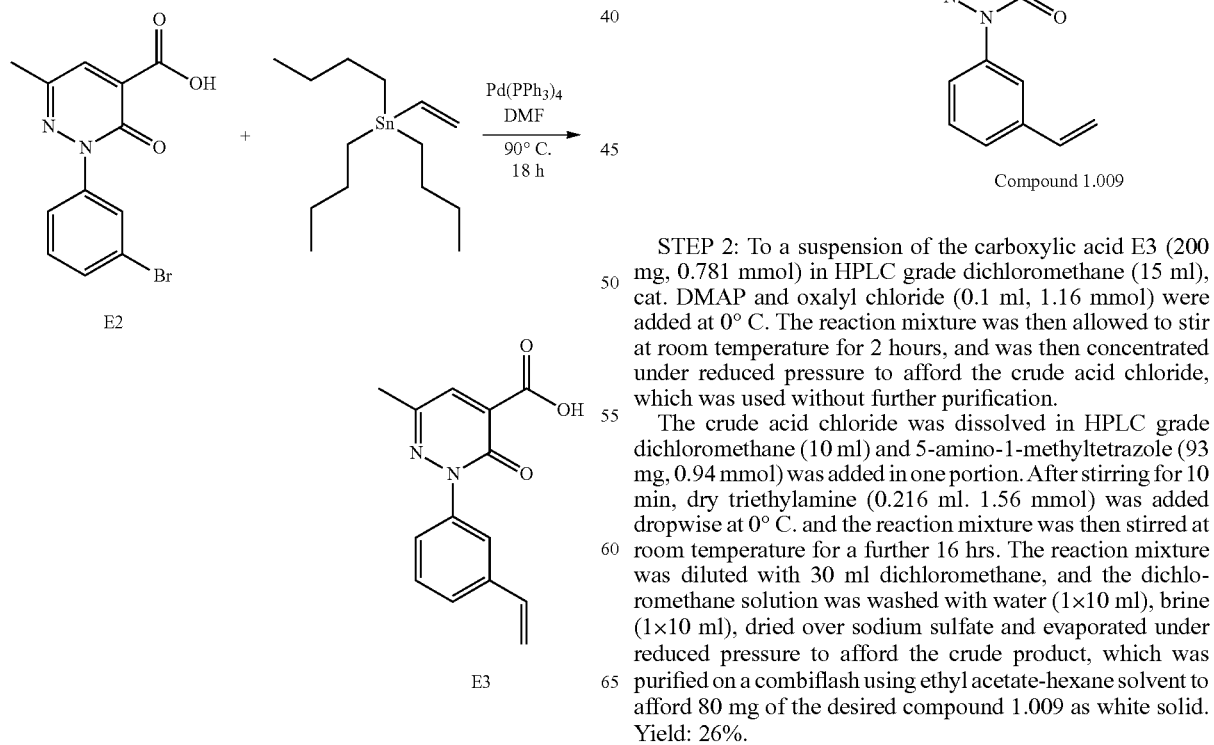

STEP 2: To a suspension of the carboxylic acid E3 (200 mg, 0.781 mmol) in HPLC grade dichloromethane (15 ml), cat. DMAP and oxalyl chloride (0.1 ml, 1.16 mmol) were added at 0° C. The reaction mixture was then allowed to stir at room temperature for 2 hours, and was then concentrated under reduced pressure to afford the crude acid chloride, which was used without further purification.

The crude acid chloride was dissolved in HPLC grade dichloromethane (10 ml) and 5-amino-1-methyltetrazole (93 mg, 0.94 mmol) was added in one portion. After stirring for 10 min, dry triethylamine (0.216 ml. 1.56 mmol) was added dropwise at 0° C. and the reaction mixture was then stirred at room temperature for a further 16 hrs. The reaction mixture was diluted with 30 ml dichloromethane, and the dichloromethane solution was washed with water (1×10 ml), brine (1×10 ml), dried over sodium sulfate and evaporated under reduced pressure to afford the crude product, which was purified on a combiflash using ethyl acetate-hexane solvent to afford 80 mg of the desired compound 1.009 as white solid. Yield: 26%.

EXAMPLE P3

Experimental Procedure for the Synthesis of Compound 1.017

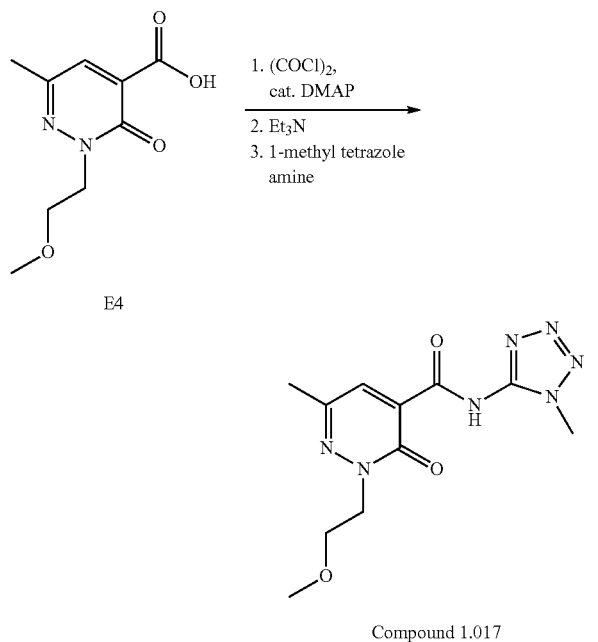

Compound 1.017

To a suspension of the carboxylic acid E4 (500 mg, 2.36 mmol) in HPLC grade dichloromethane (10 ml), cat. DMAP and oxalyl chloride (0.8 ml, 9.43 mmol) were added at 0° C. The reaction mixture was allowed to stir at room temperature for 2 hours, and was then concentrated under reduced pressure to obtain the crude acid chloride, which was used without further purification.

The crude acid chloride was dissolved in HPLC grade dichloromethane (10 ml) and 5-amino-1-methyltetrazole (230 mg, 2.36 mmol) was added in one portion. After stirring for 10 min, dry triethylamine (1.3 ml. 9.43 mmol) was added dropwise at 0° C., and the reaction mixture was allowed to stir at room temperature for 16 hrs. The reaction mixture was then diluted with 30 ml dichloromethane, and the dichloromethane solution was washed with water (1×10 ml), brine (1×10 ml), dried over sodium sulfate and evaporated under reduced pressure to afford the crude product, which was purified on a Combiflash using ethyl acetate-hexane solvent to afford the desired compound 1.017 as a white solid (170 mg). Yield: 12%.

EXAMPLE P4

Experimental Procedure for the Synthesis of Compound 1.018

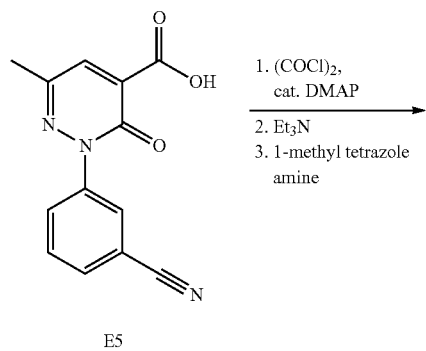

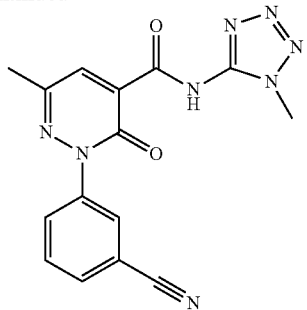

Compound 1.018

To a suspension of the carboxylic acid E5 (200 mg, 0.784 mmol) in HPLC grade dichloromethane (15 ml), cat. DMAP and oxalyl chloride (0.1 ml, 1.16 mmol) were added at 0° C. The reaction mixture was allowed to stir at room temperature for 2 hours, and was then concentrated under reduced pressure to afford the crude acid chloride, which was used without further purification.

The crude acid chloride was dissolved in HPLC grade dichloromethane (10 ml) and 5-amino-1-methyltetrazole (93 mg, 0.94 mmol) was added in one portion. After stirring for 10 min, dry triethylamine (0.216 ml. 1.56 mmol) was added dropwise at 0° C., and the reaction mixture was stirred at room temperature for a further 16 hrs. The reaction mixture was diluted with 30 ml dichloromethane, and the dichloromethane solution was washed with water (1×10 ml), brine (1×10 ml), dried over sodium sulfate and evaporated under reduced pressure to afford the crude product, which was purified on a Combiflash using ethyl acetate-hexane solvent to afford the desired compound 1.018 as a white solid (67 mg). Yield: 23%.

EXAMPLE P5

Experimental Procedure for the Synthesis of Compounds 1.021 and 1.022

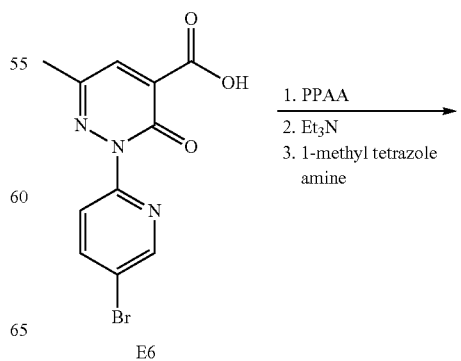

-continued

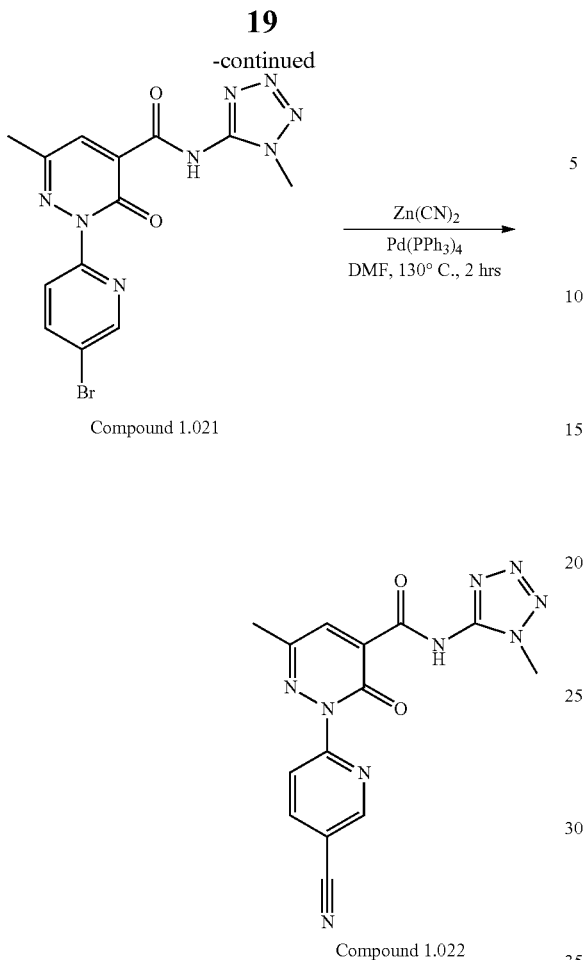

Compound 1.021

Compound 1.022

STEP 1: To a solution of the carboxylic acid E6 (100 mg, 0.323 mmol) and 5-amino-1-methyltetrazole (35 mg, 0.355 mmol) in HPLC grade dichloromethane (5 ml), dry triethylamine (0.09 ml, 0.645 mmol) was added drop wise at 0° C. and the reaction mixture was stirred at RT for 10 min. PPAA (50% in ethyl acetate, 0.3 ml, 0.484 mmol) was then added and stirring was continued for a further 2 hours. The reaction mixture was diluted with 30 ml dichloromethane, and the dichloromethane solution was washed with water (1×10 ml), brine (1×10 ml), dried over sodium sulfate and evaporated under reduced pressure to afford the crude product, which was purified on a Combiflash using ethyl acetate-hexane to afford the desired compound 1.021 as white solid (110 mg). Yield: 87%

STEP 2: To a solution of compound 1.021 (520 mg, 1.33 mmol) in DMF (10 ml), Zn(CN)2 [94 mg, 0.8 mmol] was added in one portion and the reaction mixture was degassed with $N_2$ for 10 min. Pd(PPh3)4 [231 mg, 0.2 mmol] was then added, and the reaction mixture was heated to 13° C. for 3 hours, and then allowed to cool to room temperature. The mixture was extracted with ethyl acetate (2×50 ml), and the combined ethyl acetate extracts were washed with water (1×20 ml), brine (1×10 ml), dried over sodium sulfate and evaporated under reduced pressure to afford the crude product. The ethyl acetate solution was then evaporated under reduced pressure to afford the crude product, which was purified by preparative-HPLC using acetonitrile-H2O solvent afford the desired compound 1.022 as white solid (22 mg). Yield: <10%.

EXAMPLE P6

Experimental Procedure for the Synthesis of Compound 1.023

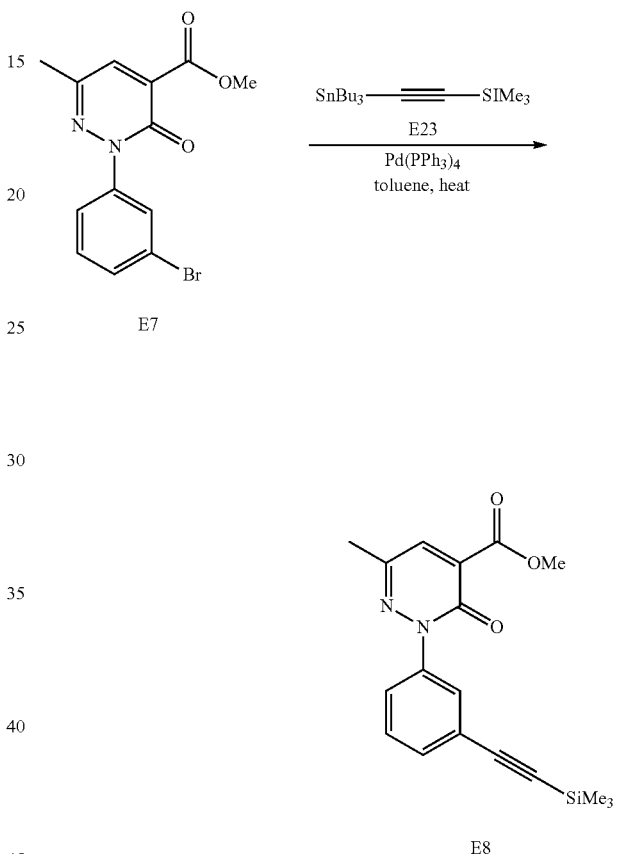

STEP 1: The pyridazinone-ester E7 (1.5 g, 40642 mmol) was dissolved in dry toluene (25 ml) in a sealed tube & degassed for 10 min. Then trimethyl(2-tributylstannylethenyl)silane E23 (2.045 ml, 5.57 mmol) was added and the solution was degassed for a further 10 min. Finally, tetrakis (triphenylphosphine)palladium(0) (536 mg, 0.464 mmol) was added and the mixture was degassed for 10 min. The reaction mixture was then stirred at 130° C. overnight, after which it was cooled to room temperature and 40% KF solution was added. The resulting mixture was stirred for 15 min. The mixture was diluted with ethylacetate & the organic extract was washed with water followed by brine. The organic layer was separated, dried over sodium sulfate, concentrated under reduced pressure, and the resulting crude product was purified by combiflash to give E8 (1.1 g, 70%).

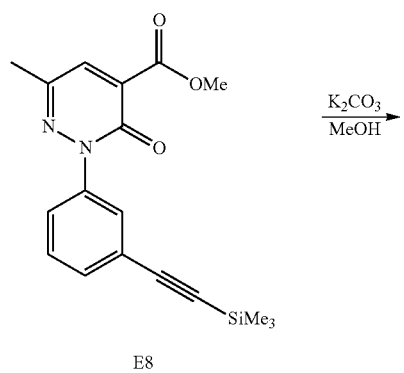

E8

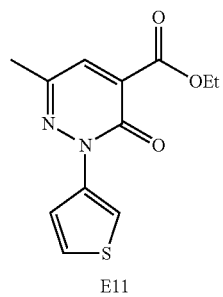

E11

STEP 1: the pyridazinone ester E10 (1.31 gm, 7.19 mmol) was dissolved in dry dichloromethane (15 ml), and dry triethylamine (1.97 ml, 14.381 mmol), dry pyridine (1.16 ml, 14.381 mmol), copper (II) acetate (2.61 gm, 14.381 mmol) were added. Molecular sieves & thiophene 3-boronic acid (1.38 gm, 10.78 mmol) were then added, and the mixture was heated to 50'C whilst air was bubbled through it. After 2 hours the mixture was cooled, and was filtered through a bed of celite. The filtrate was concentrated & purified by combiflash to give the ethyl ester E11.

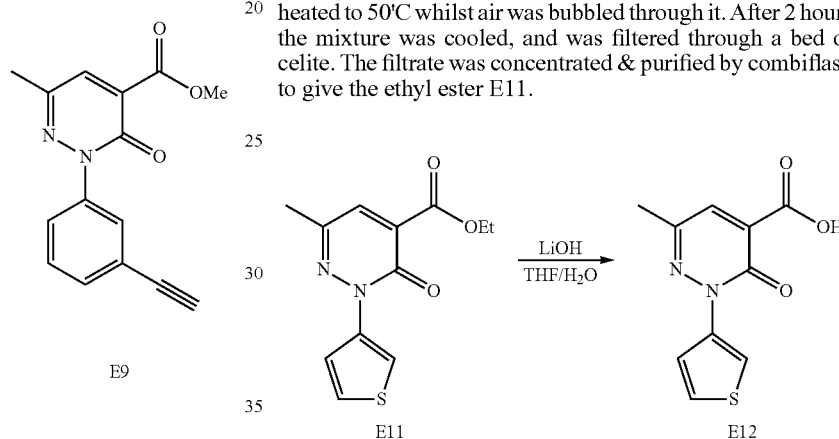

STEP 2: The silyl acetylene E8 (1.1 g, 3.231 mmol) was dissolved in methanol and potassium carbonate (89 mg, 0.646 mmol) was added. The reaction mixture was stirred at room temperature for 2 h, then the methanol was evaporated & the crude product was partitioned between dichloromethane and water. The water extract was acidified with 2 (N)HCl and extracted with dichloromethane. The dichloromethane extract was washed with brine, dried over sodium sulfate, and concentrated under reduced pressure to afford the product E9 as a brown solid (525 mg, 64%). Compound 1.023 was then produced via coupling with the appropriate 1-alkyl-5-aminotetrazole.

STEP 2: Compound E11 (1.27 g, 4.816 mmol) was dissolved in a THF-water mix (8 ml-2 ml) and the mixture was cooled to 0° C. Then lithium hydroxide (173 mg, 7.224 mmol) was added and the mixture was stirred at the same temperature for 30 min. Water was added and the mixture was extracted with dichloromethane. Then the water extract was acidified with 2 (N)HCl and again extracted with DCM. The organic extract was washed with water, brine, dried over sodium sulfate & concentrated under reduced pressure to afford the pure acid E12. Compound 1.025 was then produced via coupling with the appropriate 1-alkyl-5-aminotetrazole.

EXAMPLE P8

Experimental Procedure for the Synthesis of Compound 1.026

EXAMPLE P7

Experimental Procedure for the Synthesis of Compound 1.025

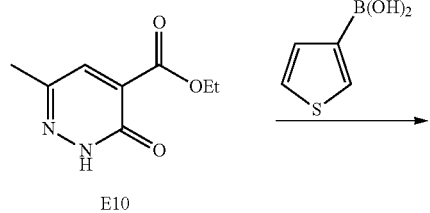

E10

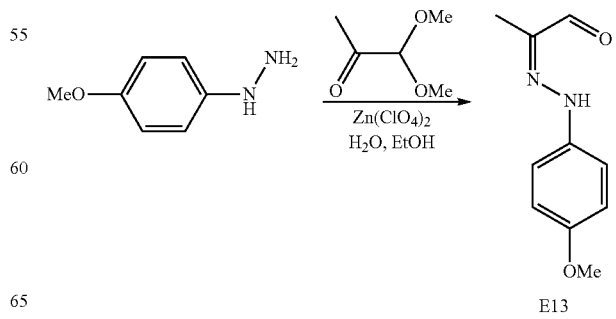

E13

STEP 1: To a suspension of (4-methoxyphenyl)hydrazine hydrochloride (29.6 g, 169 mmol, 1.00 equiv.) in water (102 mL) and ethanol (102 mL) was added 1,1-dimethoxypropan-2-one (20.0 g, 169 mmol, 1.00 equiv.) followed by zinc diperchlorate hexahydrate (1.26 g, 3.39 mmol, 0.0200 equiv.). A brown solid appeared after 10 minutes and the reaction mixture was left to stir at room temperature for 1 h. The ethanol was removed by concentrating under reduced pressure, and the residual brown solid was collected by filtration and washed with water to leave the product E13 as a brown solid that required no further purification.

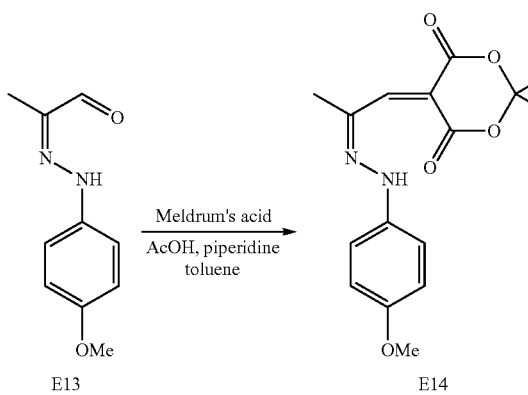

STEP 2: To a suspension of the finely crushed aldehyde E13, obtained from step 1, and 2,2-dimethyl-1,3-dioxane-4,6-dione (Meldrum's acid (fresh bottle), 25.3 g, 176 mmol) in toluene (158 mL) in a 250 ml flask was added acetic acid (1.06 g, 1.01 mL, 17.6 mmol, 0.100 equiv.) and piperidine (1.50 g, 1.74 mL, 17.6 mmol) and the reaction mixture stirred at room temperature for 18 h. After this time a deep red precipitate had formed. The red solid E14 was collected by filtration and washed with toluene.

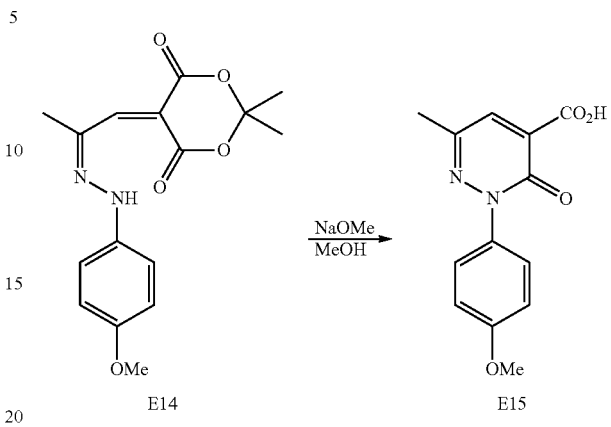

STEP 3: The red solid E14 from step 2 was suspended in methanol (298.9 mL) and sodium methoxide (25% weight) (38.71 g, 41.0 mL, 175.8 mmol) was added. The red colour disappeared, and a yellow precipitate formed. The reaction mixture became very thick and stopped stirring. Ethanol was added to the reaction mixture, and the precipitate was filtered off. This was then dissolved in water and acidified to pH 1 with 2 M aq HCl solution. A yellow solid formed, which was collected by filtration and washed with water. The solid was collected slurried with ethanol (200 ml), and the thick suspension was heated to 65 C and then cooled to rt. The resultant yellow solid was collected by filtration and dried, affording the acid E15. Compound 1.026 was then produced via coupling with the appropriate 1-alkyl-5-aminotetrazole.

TABLE 1

Examples of herbicidal compounds of the present invention.

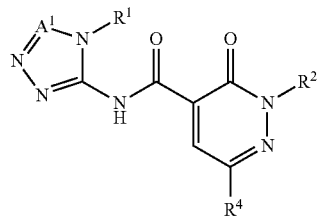

| Compound | $A^1$ | $R^1$ | $R^2$ | $R^4$ | NMR |
|---|---|---|---|---|---|
| 1.001 | N | Me | -phenyl | Me | (CDCl3) 8.39 (d, 1H), 8.28 (d, 1H), 7.62-7.51 (m, 5H), 4.05 (s, 3H), 2.27 (s, 3H). |
| 1.002 | CH | Me | -phenyl | Me | |
| 1.003 | N | Me | 2-Methylphenyl- | Me | 12.40 (1H, bs), 8.32 (1H, s), 7.41 (3H, m), 7.28 (1H, d), 4.03 (3H, s), 2.55 (3H, s), 2.19 (3H, s). |
| 1.004 | N | Me | 2-MeO-phenyl- | Me | 12.48 (1H, bs), 8.27 (1H, s), 7.51 (2H, d), 7.04 (2H, d), 4.04 (3H, s), 3.89 (3H, s), 2.56 (3H, s). |
| 1.005 | N | Me | 3,5dichlorophenyl- | Me | 12.15 (1H, bs), 8.29 (1H, s), 7.60 (2H, d), 7.49 (1H, t), 4.05 (3H, s), 2.57 (3H, s). |
| 1.006 | N | Me | 4-bromophenyl- | Me | δ6-DMSO: 11.84 (1H, s), 8.23 (1H, s), 2.76 (2H, d), 7.58 (2H, d), 3.93 (3H, s), 2.46 (3H, s). |
| 1.007 | N | Me | 3-bromophenyl- | Me | δ6-DMSO: 11.81 (1H, s), 8.24 (1H, s), 7.87 (1H, s), 7.71 (1H, d), 7.64 (1H, d), 7.53 (1H, t), 3.93 (3H, s), 2.46 (3H, s). |

TABLE 1-continued

Examples of herbicidal compounds of the present invention.

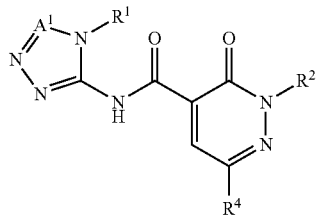

| Compound | A¹ | R¹ | R² | R⁴ | NMR |
|---|---|---|---|---|---|
| 1.008 | N | Me | 4-vinylphenyl- | Me | δ6-DMSO: 11.92 (1H, s), 8.24 (1H, s), 7.65 (2H, d), 7.58 (2H, d), 6.62 (1H, dd), 5.94 (1H, d), 5.37 (1H, d), 3.93 (3H, s), 2.46 (3H, s). |
| 1.009 | N | Me | 3-vinylphenyl- | Me | δ6-DMSO: 11.91 (1H, s), 8.24 (1H, s), 7.68 (1H, s), 7.60 (1H, d), 7.53 (1H, t), 7.50 (1H, m), 6.81 (1H, dd), 5.91 (1H, d), 5.36 (1H, d), 3.93 (3H, s), 2.46 (3H, s). |
| 1.010 | N | Me | 4-ethoxyphenyl- | Me | δ6-DMSO: 12.00 (1H, s), 8.21 (1H, s), 7.48 (2H, d), 7.05 (2H, d), 4.09 (2H, q), 3.92 (3H, s), 2.45 (3H, s), 1.36 (3H, t). |
| 1.011 | N | Me | 4-ethylphenyl- | Me | δ6-DMSO: 11.98 (1H, s), 8.21 (1H, s), 7.47 (2H, m), 7.37 (2H, m), 3.92 (3H, s), 2.70 (2H, q), 2.40 (3H, s), 2.23 (3H, t). |
| 1.012 | N | Me | 4-chlorophenyl- | Me | d6-DMSO: 11.95 (1H, s), 8.23 (1H, s), 7.64 (4H, m), 3.93 (3H, s), 2.45 (3H, s). |
| 1.013 | N | Me | 3,4difluorophenyl- | Me | δ6-DMSO: 11.78 (1H, s), 8.06 (1H, m), 7.77 (1H, t), 7.61 (1H, m), 7.48 (1H, m), 3.87 (3H, s), 2.42 (3H, s). |
| 1.014 | N | Me | 4-fluorophenyl- | Me | δ6-DMSO: 11.89 (1H, s), 8.24 (1H, s), 7.64 (2H, m), 7.39 (2H, t), 3.93 (3H, s), 2.45 (3H, s). |
| 1.015 | N | Me | 2-Cl,4-F-phenyl- | Me | δ6-DMSO: 11.71 (1H, s), 8.29 (1H, s), 7.76 (2H, m), 7.47 (1H, m), 3.93 (3H, s), 2.45 (3H, s). |
| 1.016 | N | Me | 3-fluorobenzyl | Me | δ6-DMSO: 11.97 (1H, s), 8.17 (1H, s), 7.41 (1H, q), 7.17 (3H, m), 5.41 (2H, s), 3.92 (3H, s), 2.43 (3H, s). |
| 1.017 | N | Me | MeOEt— | Me | δ6-DMSO: 12.09 (1H, bs), 8.16 (1H, s), 4.38 (2H, t), 3.94 (3H, s), 3.76 (2H, t), 3.26 (3H, s), 2.42 (3H, s). |
| 1.018 | N | Me | 3-cyanophenyl- | Me | δ6-DMSO: 11.75 (1H, bs), 8.13 (1H, s), 8.05 (1H, s), 7.96 (2H, m), 7.76 (1H, t), 3.86 (3H, s), 2.43 (3H, s). |
| 1.019 | N | Me | 2-Me,5-Cl-phenyl- | Me | δ6-DMSO: 11.84 (1H, s), 8.27 (1H, s), 7.51 (3H, m), 3.93 (3H, s), 2.45 (3H, s), 2.09 (3H, s). |
| 1.020 | N | Me | 2-Br,4-F-phenyl- | Me | δ6-DMSO: 11.70 (1H, s), 8.03 (1H, s), 7.84 (1H, m), 7.65 (1H, m), 7.47 (1H, m), 3.84 (3H, s), 2.41 (3H, s). |
| 1.021 | N | Me | 5-bromo-pyrid-2-yl- | Me | |
| 1.022 | N | Me | 5-cyano-pyrid-2-yl- | Me | δ6-DMSO: 11.90 (1H, bs), 9.14 (1H, s), 8.61 (1H, dd), 8.21 (1H, s), 7.95 (1H, d), 3.92 (3H, s), 2.45 (3H, s). |
| 1.023 | N | Me | 4-ethynylphenyl- | Me | δ (DMSO): 11.86 (1H, s); 8.24 (1H, s); 7.23 (1H, s); 7.64-7.57 (3H, complex m); 4.34 (1H, s); 3.93 (3H, s); 2.48 (s 3H). |
| 1.024 | N | Me | 3-ethynylphenyl- | Me | δ (DMSO): 2.36 (3H, s); 3.33 (3H, s); 3.81 (1H, s); 7.58 (4H, broad); 7.78 (1H, broad); 11.83 (1H, broad) |
| 1.025 | N | Me | 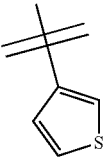 | Me | |
| 1.026 | N | Me | 4-methoxyphenyl- | Me | |

TABLE 2

Examples of herbicidal compounds of the present invention.

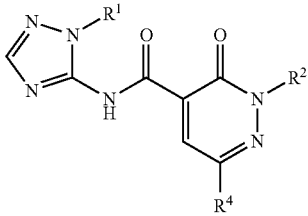

| Compound | R¹ | R² | R⁴ |
|---|---|---|---|
| 2.001 | Me | -phenyl | Me |
| 2.002 | Me | -phenyl | Me |
| 2.003 | Me | 2-Me-phenyl- | Me |
| 2.004 | Me | 2-MeO-phenyl- | Me |
| 2.005 | Me | 3,5dichlorophenyl- | Me |
| 2.006 | Me | 4-bromophenyl- | Me |
| 2.007 | Me | 3-bromophenyl- | Me |
| 2.008 | Me | 4-vinylphenyl- | Me |
| 2.009 | Me | 3-vinylphenyl- | Me |
| 2.010 | Me | 4-ethoxyphenyl- | Me |
| 2.011 | Me | 4-ethylphenyl- | Me |
| 2.012 | Me | 4-chlorophenyl- | Me |
| 2.013 | Me | 3,4difluorophenyl- | Me |
| 2.014 | Me | 4-fluorophenyl- | Me |
| 2.015 | Me | 2-Cl,4-F-phenyl- | Me |
| 2.016 | Me | 3-fluorobenzyl | Me |
| 2.017 | Me | MeOEt— | Me |
| 2.018 | Me | 3-cyanophenyl- | Me |
| 2.019 | Me | 2-Me,5-Cl-phenyl- | Me |
| 2.020 | Me | 2-Br,4-F-phenyl- | Me |
| 2.021 | Me | 5-bromo-pyrid-2-yl- | Me |
| 2.022 | Me | 5-cyano-pyrid-2-yl- | Me |
| 2.023 | Me | 4-ethynylphenyl- | Me |
| 2.024 | Me | 3-ethynylphenyl- | Me |
| 2.025 | Me | 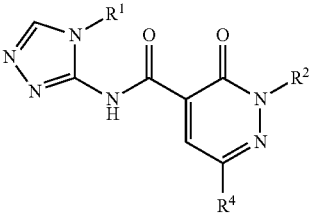 | Me |
| 2.026 | Me | 4-methoxyphenyl- | Me |

TABLE 3

Examples of herbicidal compounds of the present invention.

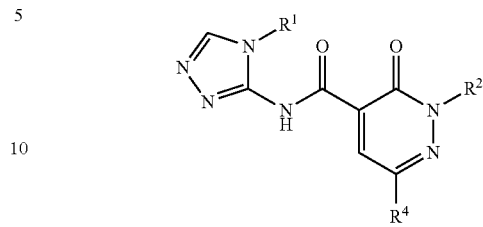

| Compound | A¹ | R¹ | R² | R⁴ |
|---|---|---|---|---|
| 3.001 | N | Me | -phenyl | Me |
| 3.002 | CH | Me | -phenyl | Me |
| 3.003 | N | Me | 2-Me-phenyl- | Me |
| 3.004 | N | Me | 2-MeO-phenyl- | Me |
| 3.005 | N | Me | 3,5dichlorophenyl- | Me |
| 3.006 | N | Me | 4-bromophenyl- | Me |
| 3.007 | N | Me | 3-bromophenyl- | Me |
| 3.008 | N | Me | 4-vinylphenyl- | Me |
| 3.009 | N | Me | 3-vinylphenyl- | Me |
| 3.010 | N | Me | 4-ethoxyphenyl- | Me |
| 3.011 | N | Me | 4-ethylphenyl- | Me |
| 3.012 | N | Me | 4-chlorophenyl- | Me |
| 3.013 | N | Me | 3,4difluorophenyl- | Me |
| 3.014 | N | Me | 4-fluorophenyl- | Me |
| 3.015 | N | Me | 2-Cl,4-F-phenyl- | Me |
| 3.016 | N | Me | 3-fluorobenzyl | Me |
| 3.017 | N | Me | MeOEt— | Me |
| 3.018 | N | Me | 3-cyanophenyl- | Me |
| 3.019 | N | Me | 2-Me,5-Cl-phenyl- | Me |
| 3.020 | N | Me | 2-Br,4-F-phenyl- | Me |
| 3.021 | N | Me | 5-bromo-pyrid-2-yl- | Me |
| 3.022 | N | Me | 5-cyano-pyrid-2-yl- | Me |
| 3.023 | N | Me | 4-ethynylphenyl- | Me |
| 3.024 | N | Me | 3-ethynylphenyl- | Me |
| 3.025 | N | Me |  | Me |
| 3.026 | N | Me | 4-methoxyphenyl- | Me |

BIOLOGICAL EXAMPLES

Seeds of a variety of test species are sown in standard soil in pots (*Alopecurus myosuroides* (ALOMY), *Setaria faberi* (SETFA), *Echinochloa crus-galli* (ECHCG), *Solanum nigrum* (SOLNI), *Amaranthus retoflexus* (AMARE), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 1000 g/h. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=80-100%; 4=60-79%; 3=40-59%; 2=20-39%; 1=0-19%).

| | POST Application | | | | | | PRE Application | | | | | |
|---|---|---|---|---|---|---|---|---|---|---|---|---|
| Compound | SOLNI | AMARE | SETFA | ALOMY | ECHCG | IPOHE | SOLNI | AMARE | SETFA | ALOMY | ECHCG | IPOHE |
| 1.001 | 5 | 4 | 3 | 5 | 5 | 4 | 5 | 5 | 3 | 5 | 4 | 3 |
| 1.003 | 5 | 5 | 3 | 4 | 5 | 5 | 4 | 5 | 3 | 2 | 5 | 4 |
| 1.004 | 5 | 5 | 5 | 5 | 5 | 5 | 5 | 5 | 5 | 5 | 5 | 4 |
| 1.005 | 5 | 5 | 5 | 5 | 5 | 5 | 5 | 5 | 5 | 5 | 5 | 5 |
| 1.006 | 5 | 5 | 5 | 5 | 5 | 4 | 5 | 5 | 5 | 5 | 5 | 5 |
| 1.007 | 5 | 5 | 5 | 5 | 5 | 5 | 5 | 5 | 5 | 5 | 5 | 3 |
| 1.008 | 5 | 5 | 5 | 5 | 5 | 5 | 5 | 5 | 5 | 5 | 4 | 2 |
| 1.010 | 5 | 5 | 5 | 5 | 5 | 5 | 5 | 5 | 5 | 5 | 5 | 4 |
| 1.011 | 5 | 5 | 5 | 5 | 5 | 5 | 5 | 5 | 5 | 5 | 5 | 4 |
| 1.012 | 5 | 5 | 5 | 5 | 5 | 5 | 5 | 5 | 5 | 5 | 5 | 3 |
| 1.013 | 5 | 5 | 5 | 5 | 5 | 5 | 5 | 5 | 5 | 5 | 5 | 4 |
| 1.014 | 5 | 5 | 5 | 5 | 5 | 5 | 5 | 5 | 5 | 5 | 5 | 4 |
| 1.016 | 5 | 5 | 1 | 4 | 4 | 3 | 5 | 5 | 5 | 2 | 4 | 4 |
| 1.017 | 5 | 5 | 5 | 5 | 5 | 5 | 5 | 5 | 5 | 5 | 5 | 5 |
| 1.018 | 5 | 5 | 5 | 5 | 5 | 5 | 5 | 5 | 5 | 5 | 5 | 5 |
| 1.019 | 5 | 5 | 5 | 5 | 5 | 5 | 5 | 5 | 5 | 5 | 5 | 5 |
| 1.020 | 5 | 5 | 5 | 5 | 5 | 5 | 5 | 5 | 5 | 5 | 5 | 5 |
| 1.022 | 5 | 5 | 5 | 5 | 5 | 4 | — | — | — | — | — | — |

The invention claimed is:

1. A compound of Formula (I):

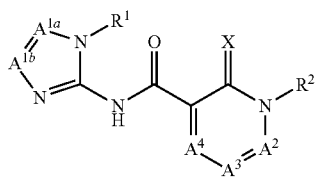

(I)

or an agronomically acceptable salt thereof,
wherein:
X is O or S;
$A^{1a}$ and $A^{1b}$ are independently selected from CH and N, wherein $A^{1a}$ and $A^{1b}$ are not both CH;
$A^2$ is N;
$A^3$ is $CR^4$;
$A^4$ is $CR^5$;
$R^1$ is selected from the group consisting of, $C_1$-$C_6$alkyl-, $C_1$-$C_6$ haloalkyl and $C_1$-$C_6$alkoxy-$C_1$-$C_3$alkyl;
$R^2$ is selected from the group consisting of hydrogen, $C_1$-$C_6$alkyl, $C_1$-$C_6$haloalkyl, $C_1$-$C_3$alkoxy-$C_1$-$C_3$ alkyl, $C_1$-$C_3$ alkoxy-$C_2$-$C_3$alkoxy-$C_1$-$C_3$-alkyl, $C_1$-$C_3$haloalkoxy-$C_1$-$C_3$-alkyl, ($C_1$-$C_3$ alkylsulfonyl-$C_1$-$C_3$ alkylamino)-$C_1$-$C_3$ alkyl, ($C_1$-$C_3$ alkylsulfonyl-$C_3$-$C_4$ cycloalkylamino)-$C_1$-$C_3$alkyl, $C_1$-$C_6$alkylcarbonyl-$C_1$-$C_3$alkyl, $C_3$-$C_6$cycloalkyl-$C_2$-$C_6$alkenyl, $C_2$-$C_6$alkynyl, $C_2$-$C_6$-alkenyl, $C_2$-$C_6$-haloalkenyl, cyano-$C_1$-$C_6$-alkyl, arylcarbonyl-$C_1$-$C_3$-alkyl, aryl-$C_1$-$C_6$alkyl, aryloxy-$C_1$-$C_6$alkyl, wherein said aryl groups may be optionally substituted with one or more substituents from the group consisting of halogen, $C_1$-$C_3$-alkoxy, $C_1$-$C_3$-alkyl, $C_1$-$C_3$ haloalkyl, and a three- to ten-membered mono- or bicyclic ring system, which may be aromatic, saturated or partially saturated and can contain from 1 to 4 heteroatoms each independently selected from the group consisting of nitrogen, oxygen and sulphur, the ring system being optionally substituted by one or more substituents selected from the group consisting of nitro, cyano, halogen, $C_1$-$C_3$alkyl, $C_1$-$C_3$haloalkyl, $C_2$-$C_3$alkenyl, $C_2$-$C_3$alkynyl, $C_1$-$C_3$ alkoxy, $C_1$-$C_3$ haloalkoxy, $C_1$-$C_6$alkyl-S(O)p- and $C_1$-$C_6$haloalkyl-S(O)p-;

$R^4$ is selected from the group consisting of hydrogen, hydroxyl, halogen, $C_1$-$C_6$alkyl, $C_1$-$C_6$haloalkyl, $C_1$-$C_6$alkoxy-$C_1$-$C_6$alkyl, $C_1$-$C_6$haloalkoxy-$C_1$-$C_6$alkyl, $C_1$-$C_6$alkoxy-$C_1$-$C_6$alkoxy-$C_1$-$C_6$alkyl, $C_1$-$C_6$alkoxy, $C_1$-$C_6$haloalkoxy, $C_1$-$C_6$alkoxy-$C_2$-$C_6$alkoxy, $C_1$-$C_6$alkylamino, $C_1$-$C_6$dialkylamino-, cyano, $C_1$-$C_6$alkyl-S(O)p- and $C_1$-$C_6$haloalkyl-S(O)$_p$—;

$R^5$ is selected from the group consisting of hydrogen, hydroxyl, $C_1$-$C_6$ alkyl, $C_1$-$C_6$haloalkyl and $C_1$-$C_6$alkoxy-$C_1$-$C_3$alkyl; and
p=0, 1 or 2.

2. The compound according to claim 1, wherein $A^{1a}$ and $A^{1b}$ are N and $R^1$ is methyl or ethyl.

3. The compound according to claim 1, wherein $R^2$ is selected from the group consisting of $C_1$-$C_6$alkyl-, $C_1$-$C_3$alkoxy-$C_1$-$C_3$alkyl-, $C_1$-$C_3$haloalkoxy-$C_1$-$C_3$alkyl-, phenyl and a 5 or 6 membered heteroaromatic ring system containing from 1 to 4 heteroatoms each independently selected from the group consisting of nitrogen, oxygen and sulphur; the phenyl or 5 or 6 heteroaromatic ring system being optionally substituted by one or more substituents selected from the group consisting of nitro, cyano, halogen, $C_1$-$C_3$alkyl, $C_1$-$C_3$haloalkyl, $C_2$-$C_3$alkenyl, $C_2$-$C_3$alkynyl, $C_1$-$C_3$ alkoxy, $C_1$-$C_3$ haloalkoxy, $C_1$-$C_6$alkyl-S(O)p- and $C_1$-$C_6$haloalkyl-S(O)p-.

4. The compound according to claim 1, wherein $R^4$ is selected from the group consisting of hydrogen, methyl and halogen.

5. The compound according to claim 1, wherein $R^5$ is hydrogen.

6. A herbicidal composition comprising a compound according to claim 1 and an agriculturally acceptable formulation adjuvant.

7. The herbicidal composition according to claim 6, further comprising at least one additional pesticide.

8. The herbicidal composition according to claim 7, wherein the additional pesticide is a herbicide or herbicide safener.

9. A method of controlling weeds at a locus comprising application to the locus of a weed controlling amount of a composition according to claim 6.

10. The compound of claim 2, wherein $R^2$ is selected from the group consisting of $C_1$-$C_6$alkyl-, $C_1$-$C_3$alkoxy-$C_1$-$C_3$alkyl-, $C_1$-$C_3$haloalkoxy-$C_1$-$C_3$alkyl-, phenyl and a 5 or 6 membered heteroaromatic ring system containing from 1 to 4 heteroatoms each independently selected from the group consisting of nitrogen, oxygen and sulphur; the phenyl or 5 or 6 heteroaromatic ring system being optionally substituted by one or more substituents selected from the group consisting of nitro, cyano, halogen, $C_1$-$C_3$alkyl, $C_1$-$C_3$haloalkyl, $C_2$-$C_3$alkenyl, $C_2$-$C_3$alkynyl, $C_1$-$C_3$ alkoxy, $C_1$-$C_3$ haloalkoxy, $C_1$-$C_6$alkyl -S(O)p- and $C_1$-$C_6$haloalkyl-S(O)p-.

11. The compound of claim 10, wherein $R^4$ is selected from the group consisting of hydrogen, methyl and halogen.

12. The compound of claim 11, wherein $R^5$ is hydrogen.

* * * * *